(12) United States Patent
Schmidt et al.

(10) Patent No.: US 7,395,105 B2
(45) Date of Patent: Jul. 1, 2008

(54) WEARABLE DEVICE FOR BIOELECTRICAL INTERACTION WITH MOTION ARTIFACT CORRECTION MEANS

(75) Inventors: Ralf Schmidt, Aachen (DE); Olaf Such, Aachen (DE); Christian Reichinger, Neutraubling (DE); Michael Perkuhn, Aachen (DE); Harald Reiter, Aachen (DE); Andras Montvay, Stuttgart (DE); Josef Lauter, Geilenkirchen (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 244 days.

(21) Appl. No.: 10/537,886

(22) PCT Filed: Dec. 8, 2003

(86) PCT No.: PCT/IB03/05805

§ 371 (c)(1),
(2), (4) Date: Jun. 7, 2005

(87) PCT Pub. No.: WO2004/052190

PCT Pub. Date: Jun. 24, 2004

(65) Prior Publication Data

US 2006/0149146 A1     Jul. 6, 2006

(30) Foreign Application Priority Data

Dec. 10, 2002    (EP)    ................... 02080213

(51) Int. Cl.
*A61B 5/04* (2006.01)
(52) U.S. Cl. ................................. 600/372
(58) Field of Classification Search .................. 600/372
See application file for complete search history.

(56) References Cited

U.S. PATENT DOCUMENTS

| 5,355,883 | A | 10/1994 | Ascher |
| 5,494,043 | A | 2/1996 | O'Sullivan et al. |
| 5,978,693 | A | 11/1999 | Hamilton et al. |
| 6,912,414 | B2 * | 6/2005 | Tong .......................... 600/372 |

* cited by examiner

*Primary Examiner*—Lee S Cohen

(57) ABSTRACT

The invention relates to a wearable device arranged for enabling a bioelectrical interaction with an individual when being brought into contact with the individual's skin I, said device comprising electrodes 2 arranged to carry out said interaction by means of a first electrical signal, said electrodes comprise motion artifact detection means 4. The electrode assembly 1 comprises electrode 2 arranged to carry out a bioelectrical interaction with the individual by means of measuring an electrical signal on the body of the individual I and/or applying an electrical signal to the body of the individual. In order to enable said bioelectrical interaction the electrode 2 is provided with an electrical cable 2a. According to the invention, the electrode 2 is arranged with a pr 4. The pressure sensor 4 is arranged to measure a normal force component of an external force applied to the electrode due to movement of the individual. Preferably the pressure sensor 4 is a force/pressure sensitive resistor or a capacitive pressure sensor. The pressure sensor is arranged to produce an electrical signal, referred to as the second signal, the magnitude of the second signal being proportional to the pressure load. The pressure sensor 4 is arranged with cables 4a, 4b for purposes of signal proce

6 Claims, 2 Drawing Sheets

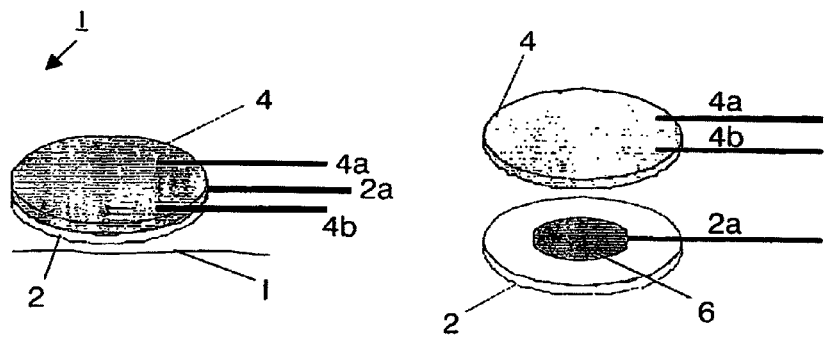
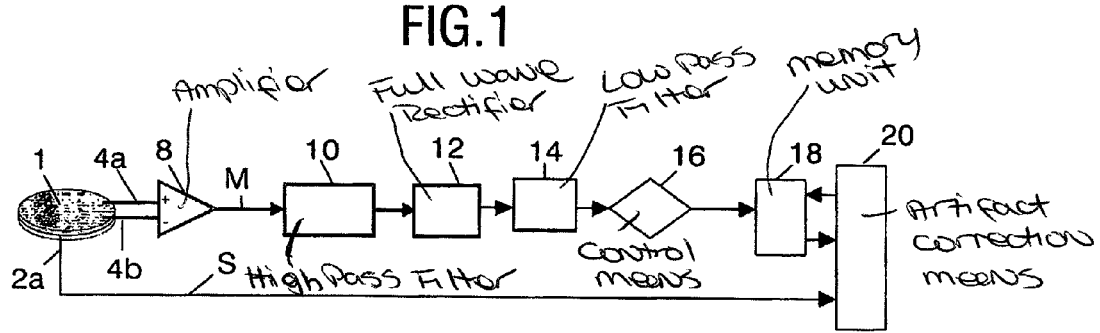
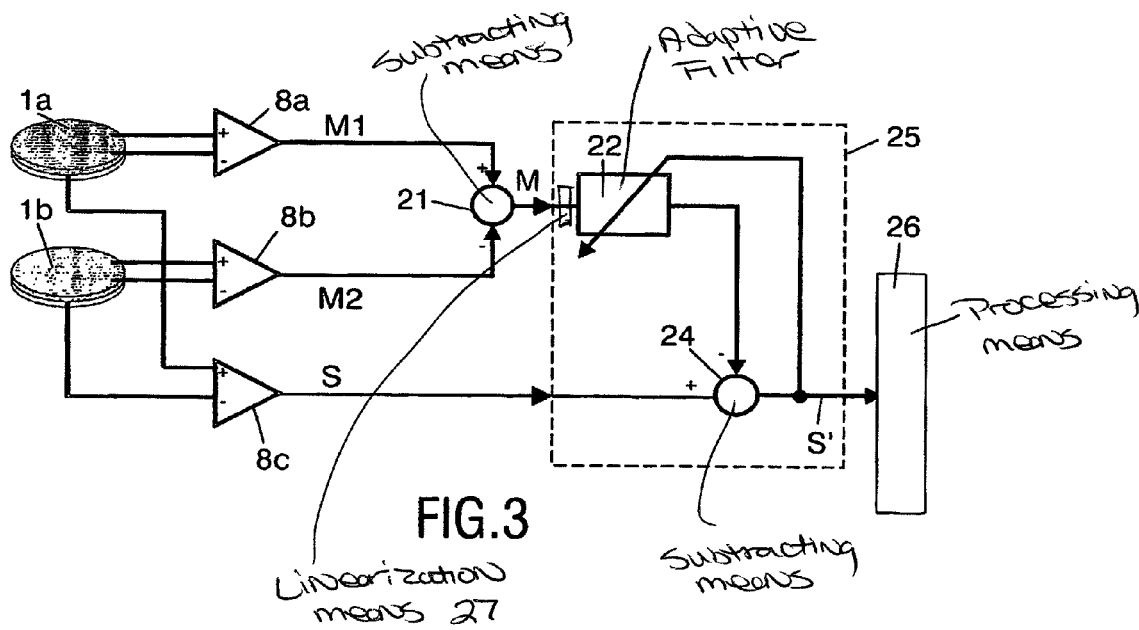
FIG.1
FIG.2
FIG.3

WEARABLE DEVICE FOR BIOELECTRICAL INTERACTION WITH MOTION ARTIFACT CORRECTION MEANS

The invention relates to a wearable device arranged for enabling a bioelectrical interaction with an individual by means of a first signal, said device comprising an electrode having a contact surface arranged to be brought into contact with the individual's skin for carrying out said interaction, the electrode comprising motion artifact detection means.

The invention further relates to an electrode assembly comprising an electrode having a contact surface, the electrode assembly being arranged to enable a bioelectrical interaction with an individual by means of a first signal when the contact surface is brought in contact with the individual's skin, said electrode assembly comprising motion artifact detection means.

An embodiment of a wearable device as set forth in the opening paragraph is known from U.S. Pat. No. 5,978,693. The known device is suited to perform a skin-mounted recording of an electrical signal from the individual by means of an electrode assembly. Such a device is suitable to carry-out a measurement of a signal related to a physiological condition of the individual. The known device is particularly suited to operate in situations when the individual is not immobilized. The signal measured on the body of the individual is further referred to as the first signal. It must be noted that the known device is also suitable to perform another type of bioelectrical interaction with the individual, namely an application of an electrical pulse to the individual's skin. Under the definitions of the current application, such an electrical pulse is also referred to as the first electrical signal. In the first embodiment of the known device the first signal is analyzed by processing means of the wearable device in order to monitor the physiological condition. The monitoring can be carried out based, for example on the absolute value, a frequency or another suitable characteristic of the first signal. In the second embodiment of the known device (application of electrical signals to the individual) the absolute value of the applied signal is determined by the processing means prior to said application. It is acknowledged in the art that motion artifacts occur when the electrodes are displaced due to movements of the individual, leading to erroneous first signal processing. The known electrode assembly comprises motion artifact detection means arranged to enable the motion artifact correction. The motion artifact detection means of the known device comprise a deformation sensor. The deformation sensor is positioned on the surface of the electrode, covering a part of the area of the electrode. A deformation in the electrode's geometry, like stretching or bending yields a signal on the deformation sensor. The processing means of the known device is arranged to carry out signal processing of the signal from the deformation sensor in order to perform the motion artifact correction.

A disadvantage of the known device is twofold. First, the motion artifact detection means is complicated in its design, adding to the manufacturing cost of the device as a whole. Secondly, the known deformation sensor is arranged to cover only a small area of the electrode assembly thus resulting in inaccuracy of artifact correction, as the signal from the deformation sensor is not always representative of the deformation in the geometry of the electrode as a whole.

It is an object of the invention to provide a wearable device where the motion artifact correction is relatively simple with reliable results.

The wearable system according to the invention is characterized in that the motion artifact detection means is arranged to determine a component normal to the contact surface of an external force applied to the electrode under operating conditions, said motion artifact detection means being arranged to provide a second signal and comprising motion artifact correction means to process the second signal in order to correct the value of the first signal for a motion artifact. The technical measure of the invention is based on the insight that the most significant motion artifacts occur from pushing on the electrodes. Therefore, normal force is a more relevant component than oblique force components. Additionally, sensors arranged to measure force are cheap and mechanically robust and can easily be attached to the electrode without sufficiently increasing the weight of the assembly. The artifact detection means of the wearable device according to the invention is arranged to measure a signal related to the normal component of the force, further referred to as the second signal. The second signal is made available to the motion artifact correction means for motion correction. After the motion correction has been carried-out the first electrical signal can be processed further leading to a more accurate interaction with the individual. In the context of the present invention the interaction with the individual comprises measuring an electrical signal on the body of the individual and/or applying an electrical signal to the body of the individual. A preferred embodiment of the measuring of an electrical signal on the body of the individual comprises a measurement of a cardiac activity of the individual. A preferred embodiment of the application of an electrical signal to the body of the individual comprises a myostimulation or an application of an electrical signal for other purposes.

An embodiment of the device according to the invention is characterized in that that the device comprises control means arranged to analyze the second signal, said control means being further arranged to actuate the motion artifact correction means upon an occurrence of a predetermined event. The wearable device according to the invention is conceived to be durably worn by the user. It is therefore preferable that the power consumption of the electronics of the wearable device is minimized. Preferably, the device according to the invention is adapted to carry out motion artifact correction only upon request. Therefore the device according to the invention is preferably arranged with control means which actuate the motion artifact correction means upon a predetermined event. An example of such a predetermined event is an actuation of a motion artifact correction button supplied on the exterior of the device. Alternatively, the motion artifact correction means can be actuated automatically by the control means in case the second signal exceeds an allowable threshold level. It is possible that more than one threshold level is assigned. For example, for each activity of the user, like sitting, walking, jogging, etc a corresponding threshold can be assigned. An actual threshold level corresponding to the actual activity of the individual can be downloaded for example from a look-up table stored in a memory unit of the device. It is possible that the type of the actual activity of the individual is set by a user interface, or is deduced from the first signal by proper signal processing. The user interface can be arranged with actuation buttons and/or voice recognition.

A further embodiment of the device according to the invention is characterized in that that the device comprises means for deriving the occurrence of the predetermined event from the second signal. The load resulting from the normal component of the external force applied to the electrodes is best assessed by a pressure sensor. The result of the force acting on the electrode is a change of the electrical potential at the boundary electrode-skin. Forces on the electrode primarily alter capacities between the electrode and the skin. A preferred embodiment of a pressure sensor is a force sensitive resistor. Due to this embodiment of the wearable device a high correlation between the force acting on the electrode and the skin potential produced by that force is determined.

A still further embodiment of the wearable device according to the invention is characterized in that the pressure sensor comprises a thin film. In order to measure the forces acting on the electrodes a thin film can be positioned on the rear surface of the electrode. Preferably, the pressure sensor comprises a thin film force/pressure sensitive resistor manufactured according to a thin film technology or a capacitive pressure sensor manufactured according to the thin film technology. The principle of operation of the said pressure sensitive sensors is known per se in the art and will not be explained in detail here. In the device according to the invention the output signal from the pressure sensor is made available to the motion artifact correction means of the device in order to perform the motion artifact reduction in the first signal by means of a suitable signal processing of the output signal from the pressure sensor. In order to carry out the motion artifact reduction accurately a calibration of relation between the output signal of the sensor and the absolute value of the motion artifact is required. In a preferred embodiment the signal processing comprises a correction for non-linearity in the relation between the absolute value of the motion artifact and the output signal from the pressure sensor. Said relation is linearized by means of a suitable signal processing. An example of such a suitable signal processing is a linearization step carried out by means of a look-up table. In case the operation of the device is controlled by a microprocessor, the estimation of a required signal linearization can be downloaded from a calibrated look-up table stored in the microprocessor of the device. The look-up table comprises non-linearity correction data for a non-linear relation between the actual value of the external force applied to the electrodes and the output signals from the pressure sensor. After the output signal from the pressure sensor is linearized the absolute value of the signal is then supplied to the motion artifact correction means. Preferably, the motion artifact correction means comprises an adaptive filter. The operation of the device will be illustrated using an example where the device according to the invention is arranged to carry out a person monitoring task. The first signal thus corresponds to a signal measured by the electrodes on the body of the individual, for example an ECG signal. In case the individual being monitored is moving, the absolute value of the first signal is distorted due to the motion artifact. The pressure sensor arranged on the rear surface of the electrodes provides the second signal which is a measure of the motion artifact. Preferably, the electrodes are of a dry type requiring no gel to be applied between the individual's skin and the measuring surface of the electrode. Suitable materials to manufacture a dry-type electrode are conducting rubber, plastic or textile. However, the output signal of the pressure sensor is not always linear with respect to the external force applied to the electrodes due to the motion. Therefore in an embodiment of the device according to the invention a signal linearization step is foreseen. Preferably, this linearization step is carried out by means of the look-up table. After the output signal from the pressure sensor is corrected for non-linearities, the absolute value of the output signal is supplied to the adaptive filter, where adaptive noise cancellation is performed. The principle of the adaptive noise cancellation is known per se in the art. Preferably a subtraction of the second signal from the first signal is carried out. Preferably, the subtraction operation is carried out digitally.

An electrode arrangement according to the invention is characterized in that the motion artifact detection means is arranged to determine a component normal to the contact surface of an external force applied to the electrode under operating conditions, said motion artifact detection means being arranged to provide a second signal, related to the external force.

These and other aspects of the invention will be explained with reference to Figures.

FIG. 1 shows schematically an embodiment of the electrode assembly according to the invention.

FIG. 2 shows schematically an embodiment of the device according to the invention comprising control means.

FIG. 3 shows schematically an embodiment of the motion artifact correction means according to the invention.

Figure 4:
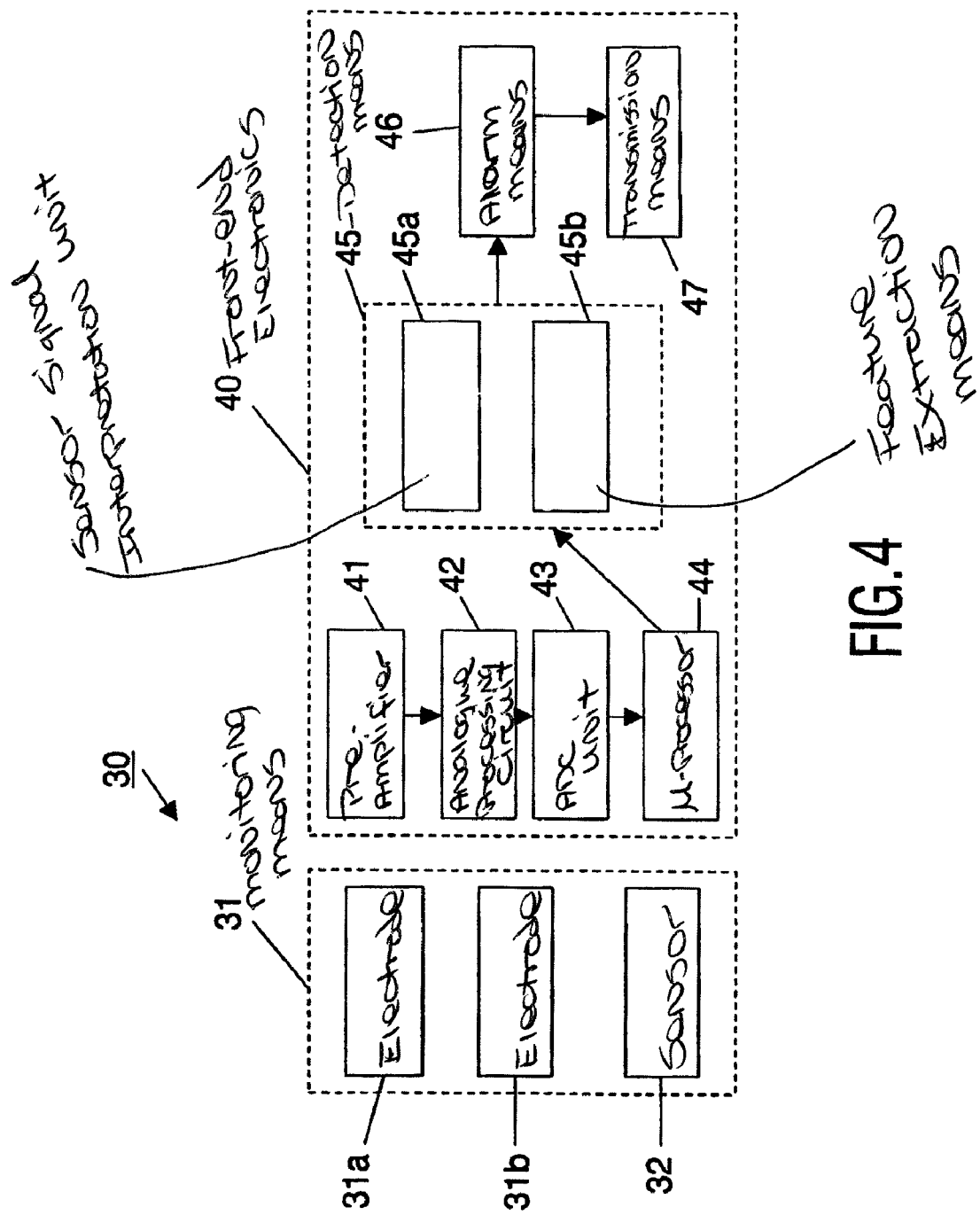
FIG. 4 shows schematically an embodiment of the wearable device according to the invention.

FIG. 1 shows schematically an embodiment of the electrode assembly according to the invention. The left-hand part of the Fig. shows an assembled electrode, whereas the right-hand part shows the components from which the electrode is assembled. The electrode assembly I comprises the electrode 2 arranged to carry out a bioelectrical interaction with the individual by means of measuring an electrical signal on the body of the individual I and/or applying an electrical signal to the body of the individual. In order to enable said bioelectrical interaction the electrode 2 is provided with an electrical cable 2a. For purposes of measuring a signal from the body of the individual, the cable 2a is connected to an input of a preamplifier followed by a suitable signal processing circuit (not shown). For purposes of an application of an electrical signal to the body of the individual, the cable 2a is connected to the output of a power supply source (not shown). The corresponding electrical circuits are known per se and fall within the scope of knowledge of the person skilled in the art. According to the invention, the electrode 2 is arranged with a pressure sensor 4. The pressure sensor 4 is arranged to measure a normal force component of an external force applied to the electrode due to movement of the individual. Preferably the pressure sensor 4 is a force/pressure sensitive resistor or a capacitive pressure sensor. The pressure sensor is arranged to produce an electrical signal, referred to as the second signal, the magnitude of the second signal being proportional to the pressure load. The pressure sensor 4 is arranged with cables 4a, 4b for purposes of signal processing.

FIG. 2 shows schematically an embodiment of the device according to the invention comprising control means. The electrode assembly I is provided with three outputs, 2a, 4a and 4b. The output 2a is a signal output from the electrode yielding the first signal S to be processed by the electronics (not shown) of the device according to the invention. The signal from the output 4a, 4b of the pressure sensor, defined previously as the second signal, is supplied to the input of an amplifier 8. The amplified signal M, characteristic to the motion artifact, is then processed by a high pass filter 10, a full wave rectifier 12 and a low pass filter 14. The resulting signal is then supplied to the input of control means 16, where the second signal is further processed. According to the invention the control means 16 is arranged to actuate the motion artifact correction means 20 upon an occurrence of a predetermined event. Examples of the predetermined event are an actuation of a motion-correction button on a user interface (not shown), an actuation of a voice recognition routine on a user interface where a demand to switch on the motion artifact correction is recognized. In a preferred embodiment the event corresponds to the second signal exceeding a predetermined threshold level. Preferably the corresponding threshold is stored in a memory unit 18. Upon an occurrence of the event the motion artifact correction means 20 are actuated and the motion artifact correction is carried out. For this purpose the first signal S and the processed second signal M are supplied to the input of the motion artifact correction means 20.

FIG. 3 shows schematically an embodiment of the motion artifact correction means according to the invention for a case where a plurality of electrode assemblies 1*a*, 1*b* are arranged on the body of the individual (not shown). The second signals M1, M2 related to the motion artifact of the electrodes 1*a* and 1*b* are amplified by means of the input amplifiers 8*a*, 8*b*. A the next step the signals M1, M2 are subtracted from each other by a first subtracting means 21 to obtain an average value of the signal to rule out electrode's differences. The resulting averaged second signal M is processed together with the first signal S by the motion artifact correction means 25, comprising an adaptive filter 22 and a second subtracting means 24. The resulting signal is the corrected first signal which is supplied to the processing means 26 of the device according to the invention. Preferably the motion artifact correction means comprises a linearization element 27 carrying out a linearization of the second signals M1 and M2. The linearized second signal is then supplied to the linear input of the adaptive filter 22.

FIG. 4 shows an embodiment of a technical realization of a wearable device according to the invention. The wearable device 30 comprises monitoring means 31 arranged to monitor a physiological condition of the user. The monitoring means 31 comprise a set of electrodes 31*a*, 31*b* to be arranged on the body of the user to pick-up a signal characteristic of the targeted physiological condition, for example an ECG signal. The electrodes 31*a* and 31*b* comprise artifact detection means [not shown] in order to provide a signal characteristic to a motion experienced by the electrodes under the operating conditions. Additionally, the monitoring means 31 can comprise a sensor 32 arranged to monitor a signal not directly related with the targeted physiological condition. An example of such a sensor is a blood pressure sensor or a respiration rate sensor. The monitoring means 31 are arranged to perform a continuous monitoring of the physiological condition of the user and are further arranged to provide a corresponding signal to the front-end electronics 40 of the system 30. The monitoring means 31 and the front-end electronics 40 are worn on the body of the user, preferably at the waist area. Examples of suitable carriers for the wearable device are known per se in the art. The front-end electronics 40 is arranged to analyze the signal from the electrodes 31*a*, 31*b*. In case the signal comprises no motion artifact it is processed as such, otherwise the front end electronics 40 performs the motion artifact correction, for example according to the embodiments shown in FIG. 2 and FIG. 3. For that purpose the front-end electronics 40 comprises a preamplifier 41 and analogue processing circuit 42, an ADC unit 43, detection means 45 and a μ-processor 44. Optionally the front-end electronics 40 comprises alarm means 46 and transmission means 47. The detection means 45 comprises a sensor signal interpretation unit 45*a* and feature extraction means 45*b*. The system 30 operates as follows: the monitoring means 31 acquires the raw data which are delivered to the front-end electronics 40. The front-end electronics 40 provides means for receiving the signals from the monitoring means, performs suited analogue processing by means of the analogue processing circuit 42. Here the signal from the electrodes is tested on motion artifact. In case the signal from the pressure sensor indicates that the artifact is acceptable, the signal from the electrodes is processed as such. Otherwise, the signal from the pressure sensor is used to correct the running value of the signal from the electrodes. The processed raw data is converted into a digital format by means of the ADC 43 and is forwarded by a μ-processor 44 to the detection means 45, where the condition of the user is being analyzed. For cardiac applications the detection means 45 comprise a per-se known QRS-detector to determine R-R peak intervals in heart cycles. The detection means 45 comprise a sensor signal interpretation unit 45*a* arranged to derive a feature in the signal characteristic of an abnormal physiological condition of the user. For cardiac applications, for example said feature can be a frequency of the signal. In case the detection means 45 detects the abnormal condition, a signal is sent to the alarm means 46 to generate an alarm, which is transmitted by the transmitting means 47, for example by means of a RF-link to warn a bystander or specialized medical personnel.

The invention claimed is:

1. A wearable device arranged for enabling a bioelectrical interaction with an individual by means of a first signal, said device comprising:
an electrode having a contact surface arranged to be brought into contact with the individual's skin for carrying out said interaction, the electrode comprising motion artifact detection means having a thin film pressure sensor arranged on a rear surface of the electrode, said rear surface being opposite the contact surface, wherein the motion artifact detection means is arranged to determine a component normal to the contact surface of an external force applied to the electrode under operating conditions, said motion artifact detection means being arranged to provide a second signal and comprising motion artifact correction means to process the second signal in order to correct the value of the first signal for a motion artifact.

2. A wearable device according to claim 1, wherein the device comprises control means arranged to analyze the second signal , said control means being further arranged to actuate the motion artifact correction means upon an occurrence of a predetermined event.

3. A wearable device according to claim 2, wherein the device comprises means for deriving the occurrence of the predetermined event from the second signal.

4. A wearable device according to claim 1, wherein the motion artifact correction means comprises a linearization element, said linearization element being arranged to correct for a non-linearity in a relation between an absolute value of the second signal and the external force.

5. A wearable device according to claim 1, wherein the electrodes are of a dry type.

6. An electrode assembly comprising:
an electrode having a contact surface, the assembly being arranged to enable a bioelectrical interaction with an individual by means of a first signal when the contact surface is brought in contact with the individual's skin, said electrode assembly comprising motion artifact detection means having a thin film pressure sensor arranged on a rear surface of the electrode, said rear surface being opposite the contact surface, wherein the motion artifact detection means is arranged to determine a component normal to the contact surface of an external force applied to the electrode under operating conditions, said motion artifact detection means being arranged to provide a second signal, related to the external force.

\* \* \* \* \*